United States Patent
Grekin

(10) Patent No.: US 6,177,105 B1
(45) Date of Patent: Jan. 23, 2001

(54) LYCD COMPOSITIONS AND THERAPY

(76) Inventor: Steven K. Grekin, 1350 Lochridge, Bloomfield Hills, MI (US) 48302

(*) Notice: Under 35 U.S.C. 154(b), the term of this patent shall be extended for 0 days.

(21) Appl. No.: 09/250,890

(22) Filed: Feb. 16, 1999

Related U.S. Application Data

(63) Continuation-in-part of application No. 09/027,237, filed on Feb. 20, 1998, now abandoned.
(51) Int. Cl.⁷ .................................................... A61K 35/12
(52) U.S. Cl. ........................... 424/520; 424/401; 424/60; 424/61; 424/63; 424/64; 424/78.02
(58) Field of Search ................................ 424/60, 61, 63, 424/64, 401, 520, 78.02; 514/714

(56) References Cited

U.S. PATENT DOCUMENTS

| | | |
|---|---|---|
| 4,942,031 | 7/1990 | Levin . |
| 5,384,123 | 1/1995 | Metsada . |
| 5,520,919 | 5/1996 | Lerner . |
| 5,569,670 | 10/1996 | Weischer et al. . |
| 5,709,868 | 1/1998 | Perricone . |
| 5,776,441 | 7/1998 | Scancarella et al. . |

*Primary Examiner*—Marianne P. Allen
(74) *Attorney, Agent, or Firm*—Dobrusin Darden Thennisch & Lorenz PLLC

(57) ABSTRACT

The present invention discloses compositions and methods for rejuvenating human skin by stimulating growth of new collagen. The topically applied compositions contain live yeast cell derivative (LYCD), and one or more natural skin supplements that, it is believed, work synergistically to create new collagen, which improves the appearance and texture of skin. A number of compositions are disclosed including formulations for an oxygenating serum, a moisturizing cream, and a facial peel. These compositions can be used in concert as part of a skin rejuvenation system.

2 Claims, No Drawings

LYCD COMPOSITIONS AND THERAPY

RELATED APPLICATION

This application is a continuation-in-part of U.S. application Ser. No. 09/027,237, filed Feb. 20, 1998 now abandoned.

BACKGROUND OF THE INVENTION

1. Field of the Invention

The present invention relates to compositions for promoting growth of collagen in human skin, and more particularly, to topical preparations containing live yeast cell derivative (LYCD).

2. Discussion

At least since the time of Cleopatra, people have applied substances to their skin in an attempt to appear younger. While many of these substances did little to improve the appearance of skin, most of the clinically proven treatments for rejuvenating skin—$\alpha$- and $\beta$-hydroxy acids, retinoic acid, chemical peels, dermabrasions, laser resurfacings—have involved substantial irritation of the skin. For example, people who use hydroxy acids or retinoic acid often complain of erythema (redness), burning, stinging, and peeling.

Moreover, it appears that skin irritation is not simply a side effect of these treatments, but is necessary for their efficacy. For example, physicians' attempts to create products and procedures that reduce the side effects of chemical treatments were accompanied by a diminution of efficacy. Similarly, though many physicians have switched from harsh $CO_2$ laser resurfacing to "gentle" erbium lasers, they report that skin rejuvenation occurs only with comparable skin destruction Current "irritant-based" treatments suffer other drawbacks. For example, the effectiveness of these treatments appears to diminish with long-term exposure or increased use. Research suggests that prolonged exposure to retinoic acid, $\alpha$- and $\beta$-hydroxy acids, and phenolic peels does not result in a continual improvement in skin appearance. A similar drawback occurs with $CO_2$ laser resurfacing, where physicians have noted that skin rejuvenation results only from moderate skin destruction. If aggressive laser destruction is performed in an attempt to correct severe skin damage, scarring can develop.

In recent years, physicians have begun exploring ways to improve skin appearance without irritation, but their efforts have met with limited success. For example, U.S. Pat. No. 4,942,031 discloses topical preparations containing live yeast cell derivative (LYCD) for reducing skin wrinkles. However, the disclosed anti-wrinkling compositions also contain retinoic acid, which, as discussed above, can irritate the skin. Another therapy, which is described in U.S. Pat. No. 5,709,868, discloses treating skin with lipoic acid but not in combination with LYCD. Moreover, the formulations disclosed in the latter patent focus on free radical scavenging and therefore do not target the result of the present invention—stimulation of collagen growth to rejuvenate skin. Thus, although the '868 patent may arguably improve skin appearance, it does so in a substantially different way than the present invention.

The present invention is directed to overcoming, or at least minimizing, one or more problems described above by using a synergistic combination of components, including LYCD.

SUMMARY OF THE INVENTION

The present invention provides topical preparations and therapies for rejuvenating skin by stimulating collagen growth. Compared to traditional skin therapies involving treatment with harsh chemicals or lasers, the present invention provides improved skin appearance and texture with less skin irritation.

In accordance with one aspect of the present invention, there is provided a topically applied serum comprising an aqueous solution of live yeast cell derivative (LYCD) and $\alpha$-lipoic acid, or a pharmaceutically acceptable salt or ester of $\alpha$-lipoic acid. The components of the serum are present in amounts effective to stimulate growth of new collagen fiber, which improves the appearance and texture of human skin.

In accordance with a second aspect of the present invention, there is provided a skin peel composition comprising an aqueous solution of LYCD and zinc acetate. The components of the skin peel composition are present in amounts effective to stimulate growth of new collagen fiber, which improves the appearance and texture of human skin.

In accordance with a third aspect of the present invention, there is provided a topically applied moisturizing cream comprising an aqueous mixture of LYCD and a hydrating agent. The hydrating agent is composed of tocopherol, tocopherol acetate or tocotrienol, either alone or in combination. The LYCD and the hydrating agent are present in amounts effective to stimulate growth of new collagen fiber, which improves the appearance and texture of human skin.

In accordance with a fourth aspect of the present invention, there is provided a method of rejuvenating human skin by stimulating growth of new collagen fiber. The method comprises the step of removing the outermost layers of skin using a skin peel composition comprising an aqueous solution of LYCD and zinc acetate. The method also includes the steps of hydrating the skin using a moisturizing cream comprising an aqueous mixture of LYCD and a hydrating agent, and oxygenating the skin using a serum comprising an aqueous mixture of LYCD and $\alpha$-lipoic acid, or a pharmaceutically acceptable salt or ester of $\alpha$-lipoic acid. The components of the peel solution, the moisturizing cream, and the serum are present in amounts effective to stimulate the growth of collagen in the skin. The hydrating agent is composed of tocopherol (vitamin E) or tocotrienol, either alone or in combination.

DESCRIPTION OF THE PREFERRED EMBODIMENTS

The compositions disclosed herein for rejuvenating human skin by stimulating collagen growth in human skin, all contain effective amounts of live yeast cell derivative (LYCD) in combination with $\alpha$-lipoic acid (6,8-dithiooctanoic acid), or pharmaceutically acceptable salts or esters of $\alpha$-lipoic acid, a hydrating agent, or zinc acetate. Suitable hydrating agents include tocopherol—vitamin E in its various forms, including the acetate—and tocotrienol, either alone or in combination.

LYCD and $\alpha$-lipoic acid stimulate new collagen fiber growth, which improves the appearance and texture of skin. While not wishing to be bound by any particular theory, it appears that LYCD stimulates collagen growth by providing a necessary precursor—oxygen —while $\alpha$-lipoic acid is added specifically to increase cellular activity, including the rate of collagen growth, by stimulating mitochondrial activity in the skin. Tocopherol and/or tocotrienol hydrate the skin and, along with zinc acetate, help transport LYCD through the outer skin layers to the basal cells where collagen fiber growth occurs.

LYCD is a skin respiratory factor derived from *Saccharomyces cerevisiae*, and is known to stimulate collagen growth. It is purified and produced by a complex fermentation process and is available from many producers including Langer Laboratories, a subsidiary of Sperti Drug Co., MDH Laboratories, Inc., and Universal Foods Corporation. LYCD is typically quantified in terms of Skin Respiratory Factor (SRF) units. One SRF unit is the amount needed to increase the oxygen uptake of 1 mg of dry weight rat abdominal skin by 1 percent at the end of a 1 hour testing period in a Warburg apparatus.

A first embodiment—a topically applied serum—is disclosed in Table 1. The serum contains 4 wt. % LYCD and 4 wt. % α-lipoic acid, although both components can be used at levels as low as about 1 wt. %. LYCD and α-lipoic acid can each be used at levels up to about 10 wt. % without adverse effects, but when LYCD and α-lipoic acid are used in amounts substantially greater than about 4 wt. %, there is believed to be little increase in the effectiveness of the serum. Although the weight ratio of LYCD to α-lipoic acid can vary from about 10:1 to about 1:10, LYCD and α-lipoic acid are typically employed at about a one-to-one weight ratio. In addition to the free acid, one may use pharmaceutically acceptable salts and esters of α-lipoic acid. The balance of the ingredients listed in Table 1 improve transport of the active ingredients through the outer skin layers to the basal cells (propylene glycol and zinc acetate), increase the viscosity and thicken the serum (hydroxymethylcellulose and methylparaben, respectively), or stabilize active ingredients (imidazolidinyl urea).

To rejuvenate skin, the serum disclosed in Table 1 is applied about once a day, typically at bedtime, though the frequency and timing of the applications may vary. The serum is applied to a dry face, with upward and outward strokes. It is believed that most patients will notice an improvement in skin texture and appearance in about two weeks. Few patients should report the discomfort or irritation associated with more harsh chemical treatments such as retinoic acid.

TABLE 1

| LYCD Serum | |
| --- | --- |
| Chemical Name | Wt. % |
| De-ionized Water | 86.8399 |
| Hydroxyethylcellulose | 1.2000 |
| Propylene Glycol USP | 3.5000 |
| Methylparaben | 0.2000 |
| Imidazolidinyl Urea | 0.2000 |
| LYCD (2000–4000 units/mg) | 4.0000 |
| Zinc Acetate | 0.0001 |
| a-lipoic acid | 4.0000 |
| Fragrance | 0.0600 |

Table 2 lists components of an aqueous peel solution, which contains 2.9 wt. % LYCD and 1 wt. % zinc acetate. The relatively high concentration of zinc acetate helps ensure rapid transport of LYCD to the basal cells. As with the LYCD serum disclosed in Table 1, the aqueous peel solution can employ LYCD at levels as low as about 1 wt. % and still remain effective. In addition, the live yeast cell derivative can comprise 10 wt. % or more of the peel solution without adverse effects, though LYCD levels greater than about 4 wt. % show little increased effectiveness.

The peel solution is applied about once a month. It is applied to skin following serial application of a defatting agent, such as natural witch hazel, and a natural exfoliating solution. The exfoliating agent comprises an aqueous solution of about 2 wt. % papain and about 1 wt. % bromelin and is available from 220 Laboratories, Riverside, Calif. It chemically breaks bonds between keratinocytes (dead skin cells) and facilitates penetration of the peel solution to level of the dermis. The peel solution is left in place for about 15 minutes and then removed with tap water. The duration and frequency of treatment can be varied depending on, for example, skin type, as well as the general health, age, and appearance of the skin prior to treatment. It is believed that some patients will notice an improvement in skin texture—decreased puffiness under the eyes, for example—within as little as five minutes after application. Over time, most patients should show improved skin texture and appearance, including less noticeable pores, fewer pimples, and so on. Few patients, if any, should experience discomfort or irritation, although the skin might appear slightly pink immediately following removal of the peel.

TABLE 2

| LYCD Peel Solution | |
| --- | --- |
| Chemical Name | Wt. % |
| De-ionized Water | 95.23 |
| LYCD (2000–4000 units/mg) | 2.90 |
| Zinc Acetate | 1.00 |
| Methylparaban | 0.87 |

Table 3 lists components of a moisturizing cream containing 4 wt. % LYCD and 5 wt. % tocopherol acetate. As discussed above, tocopherol acetate hydrates the skin and helps transport LYCD through the outer skin layers to the basal cells where collagen growth occurs. The amount of tocopherol (vitamin E) can vary. For example, the weight ratio of LYCD to tocopherol can range from about 10:1 to about 1:10, though tocopherol is typically employed at about the same level as LYCD. Like LYCD, tocopherol can be used at a level of about 10 wt. % or higher without adverse effects. Tocotrienol can be used in place of tocopherol or in addition to tocopherol, where tocotrienol refers to analogs of vitamin E—α-, β-, γ- and δ-tocopherol— in which the aliphatic moiety is unsaturated. The other components listed in Table 3 help transport LYCD through the outer skin layers or act as stabilizers, thickeners, and so on.

The moisturizing cream is applied about once a day, typically in the morning. As with the serum disclosed in Table 1, the frequency and timing of the application can vary. The moisturizing cream is applied to a dry face, and gently worked into the skin. Patients using the moisturizing cream should notice an improvement in skin texture and appearance within a few weeks; few, if any, should experience discomfort or irritation.

TABLE 3

| LYCD Moisturizing Cream | |
| --- | --- |
| Chemical Name | Wt. % |
| De-ionized Water | 68.7799 |
| Xanthan Gum | 0.1000 |
| Propylene Glycol USP | 5.0000 |
| Methylparaben | 0.2500 |
| Caprylic/Capric Triglyceride | 5.0000 |
| Squalane | 2.0000 |
| Dimethicone 225 | 0.8000 |
| Stearic Acid | 1.8000 |
| Cetearyl Alcohol | 2.1000 |
| Cetereth-20 | 2.0000 |

TABLE 3-continued

LYCD Moisturizing Cream

| Chemical Name | Wt. % |
| --- | --- |
| Tocopherol Acetate | 5.0000 |
| Propylparaben | 0.1000 |
| LYCD (4000 units/mg) | 4.0000 |
| Zinc Acetate | 0.0001 |
| Fragrance/Colorant | 3.0700 |

It is believed that the disclosed compositions will be more effective when used as part of a skin rejuvenation system. The system includes: cleansing the skin; removing the outermost skin layers about once a month using an aqueous peel solution containing LYCD and zinc acetate; hydrating the skin using a moisturizing cream containing LYCD and a hydrating agent; and oxygenating the skin using a serum containing LYCD and α-lipoic acid, or a pharmaceutically acceptable salt or ester of α-lipoic acid. The hydrating agent of the hydrating step is tocopherol, an acetate of tocopherol, or tocotrienol, either alone or in combination. Suitable aqueous peel, moisturizing cream, and oxygenating serum are disclosed in Table 2, 3, and 1, respectively.

EXAMPLES

The follow examples are intended as illustrative and non-limiting, and represent specific embodiments of the present invention.

Example 1

Twenty five patients are treated with an oxygenating serum comprising 4 wt. % LYCD and 4 wt. % α-lipoic acid. The patients are asked to apply the serum daily for five months. Photographs of each patient are taken prior to treatment and at the end of the five-month treatment period. A six-member panel composed of two physicians, two registered nurses, and two medical assistants are enlisted to compare photographs of patients taken before and after treatment. The photographs are evaluated using a five-point numerical scale: "1" indicating no change, and "2"–"5" indicating, respectively, minimal change, moderate change, substantial change, and extreme change. Change is defined as reduction in wrinkles, scars, and rough texture. Ratings for the 25 patients are averaged, resulting in a mean score of 3.76 and a median score of 4.0. No patient photograph comparisons at the end of the five-month treatment are scored at two points or less; three patient photograph comparisons receive scores of five.

Example 2

The same patients identified in Example 1 are asked to evaluate results of their treatment. At the end of the five-month treatment period, each of the patients completes an evaluation form. Each written evaluation is assigned a numerical score by one member of the photograph review panel described in Example 1. On average, the patients report a moderate to substantial change in appearance of wrinkles and fine lines. None of the 25 patients report allergic reactions, contact dermatitis or acneoform eruptions.

Example 3

A 40 year old woman with a 20 year history of dry facial skin reports an 85% improvement in skin hydration with daily application for five months of a moisturizer containing 5 wt. % tocotrienol and 4 wt. % LYCD. She reports that this improvement is substantially greater than her previous experience using moisturizers containing Vitamin E.

Example 4

A 39 year old female is plagued by severe acne scars. After four monthly treatments with an aqueous peel solution containing 2.9 wt. % LYCD and 1 wt. % zinc acetate, there is a complete resolution of superficial scars, and significant clearing of deep scars.

Example 5

A 32 year old female complains of premature deep under-eye wrinkles. The wrinkles are no longer visible after five monthly treatments with an aqueous peel solution containing 2.9 wt. % LYCD and 1 wt. % zinc acetate, and concurrent nightly application of an oxygenating serum containing 4 wt. % LYCD and 4 wt. % α-lipoic acid and morning application of a moisturizing cream containing 5 wt. % tocotrienol and 4 wt. % LYCD.

It should be understood that the above disclosure is intended to be illustrative and not restrictive. Many embodiments will be apparent to those of skill in the art upon reading the above disclosure. The scope of the invention should, therefore, be determined with reference to the appended claims, along with the full scope of equivalents to which such claims are entitled.

What is claimed is:

1. A method of rejuvenating human skin comprising the steps of:
    a) about once a month, removing layers of outermost skin using a first discrete composition comprised of an aqueous solution of a live yeast cell derivative and zinc acetate, the live yeast cell derivative and the zinc acetate present in amounts sufficient to stimulate collagen growth in human skin;
    b) contacting the remaining skin with a second discrete composition comprised of an aqueous solution of live yeast cell derivative and a hydrating agent in a cream base, the live yeast cell derivative and the hydrating agent present in said second discrete composition in amounts sufficient to stimulate collagen growth in human skin; and
    c) contacting the skin with a third discrete composition of an aqueous solution of live yeast cell derivative and α-lipoic acid, or pharmaceutically acceptable salt or ester thereof, said live yeast cell derivative and the α-lipoic acid, or pharmaceutically acceptable salt or ester thereof, present in said third discrete composition in amounts sufficient to stimulate collagen growth in human skin;
    wherein the hydrating agent of the second discrete composition is an acetate of tocopherol, tocotrienol or a mixture thereof; and
    further wherein at least one of said contacting steps (b) or (c) is performed about once a day, and wherein said removing step (a) is carried out about once a month.

2. The method of rejuvenating human skin of claim 1, wherein the removing step (a) further comprises the steps of:
    prior to removing layers of outermost skin, defatting the skin; and
    then applying an enzymatic exfoliating agent adapted to break bonds between keratinocytes.

* * * * *